(12) United States Patent
Feldman et al.

(10) Patent No.: US 8,620,398 B2
(45) Date of Patent: Dec. 31, 2013

(54) REFERENCE ELECTRODES HAVING AN EXTENDED LIFETIME FOR USE IN LONG TERM AMPEROMETRIC SENSORS

(75) Inventors: Benjamin J. Feldman, Oakland, CA (US); Zenghe Liu, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1132 days.

(21) Appl. No.: 12/131,740

(22) Filed: Jun. 2, 2008

(65) Prior Publication Data

US 2009/0294306 A1    Dec. 3, 2009

(51) Int. Cl.
*A61B 5/05*    (2006.01)
(52) U.S. Cl.
USPC ..................... 600/345; 600/372; 600/373
(58) Field of Classification Search
USPC ........................... 600/345, 372, 373
See application file for complete search history.

(56) References Cited

U.S. PATENT DOCUMENTS

| | | | |
|---|---|---|---|
| 4,909,908 A | 3/1990 | Ross et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,320,715 A | 6/1994 | Berg | |
| 5,593,852 A | 1/1997 | Heller et al. | |
| 6,175,752 B1 * | 1/2001 | Say et al. | 600/345 |
| 6,424,847 B1 | 7/2002 | Mastrototaro et al. | |
| 6,650,471 B2 | 11/2003 | Doi | |
| 6,746,582 B2 | 6/2004 | Heller et al. | |
| 2003/0135100 A1 * | 7/2003 | Kim et al. | 600/365 |
| 2004/0186365 A1 | 9/2004 | Jin et al. | |
| 2004/0258571 A1 * | 12/2004 | Lee et al. | 422/100 |
| 2005/0154271 A1 * | 7/2005 | Rasdal et al. | 600/347 |
| 2006/0258929 A1 | 11/2006 | Goode, Jr. et al. | |

* cited by examiner

*Primary Examiner* — Melanie Y Brown
(74) *Attorney, Agent, or Firm* — Edward J. Baba; Khin K. Chin; Bozicevic, Field & Francis LLP

(57) ABSTRACT

The present application provides Ag/AgCl based reference electrodes having an extended lifetime that are suitable for use in long term amperometric sensors. Electrochemical sensors equipped with reference electrodes described herein demonstrate considerable stability and extended lifetime in a variety of conditions.

17 Claims, 13 Drawing Sheets

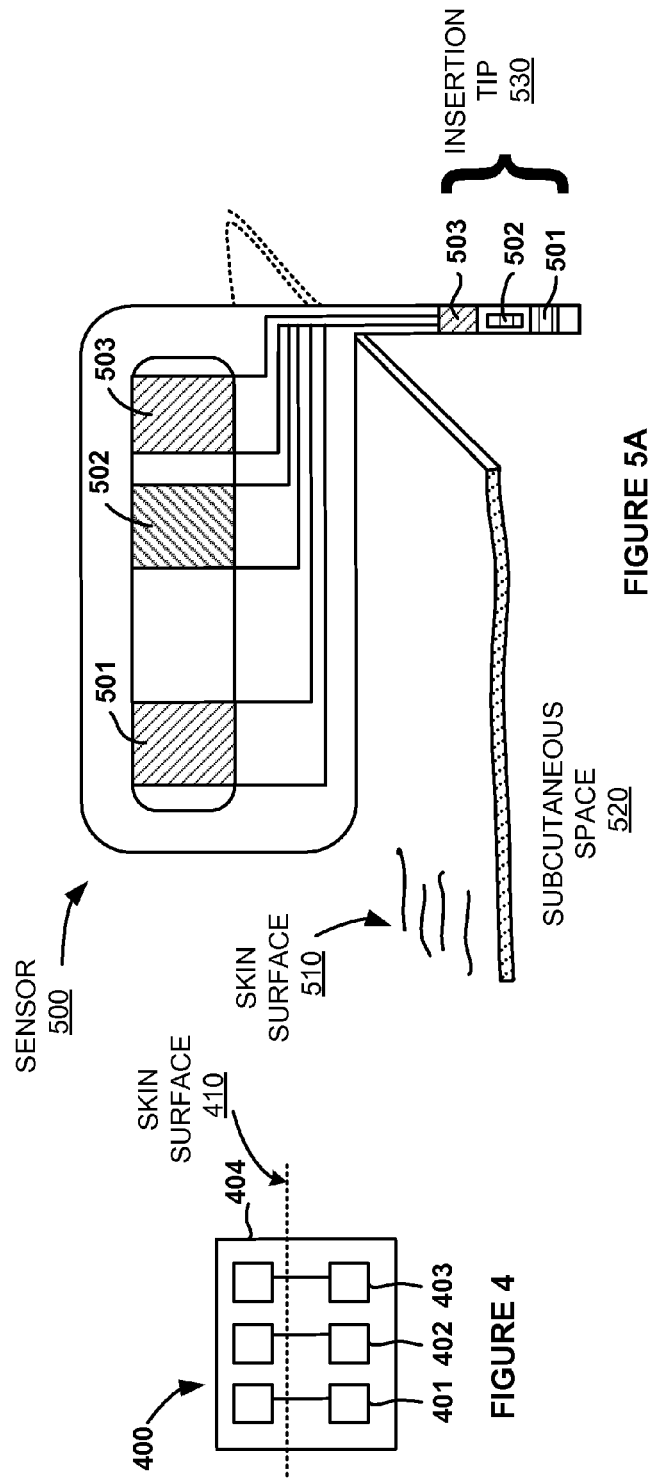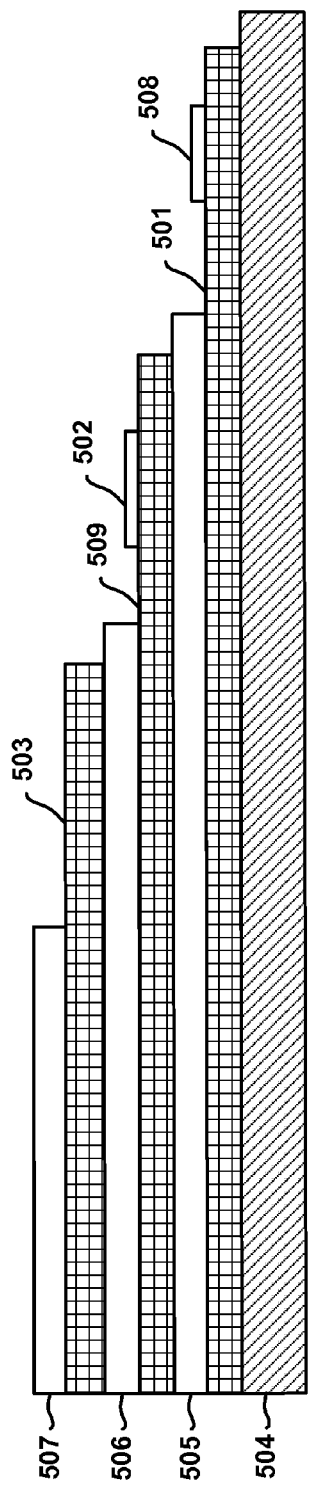

REFERENCE ELECTRODES HAVING AN EXTENDED LIFETIME FOR USE IN LONG TERM AMPEROMETRIC SENSORS

BACKGROUND OF THE INVENTION

Enzyme-based biosensors are devices in which an analyte-concentration-dependent biochemical reaction signal is converted into a measurable physical signal, such as an optical or electrical signal. Such biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. The detection of analytes in biological fluids, such as blood, is important in the diagnosis and the monitoring of many diseases.

Biosensors that detect analytes via electrical signals, such as current (amperometric biosensors) or charge (coulometric biosensors), are of special interest because electron transfer is involved in the biochemical reactions of many important bio-analytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, then the hydrogen peroxide is electrooxidized and correlated to the concentration of glucose in the body fluid.

Some biosensors are designed for implantation in a living animal body, such as a mammalian or a human body, merely by way of example. Typically, such biosensors have a three-electrode system provided with working electrodes which sensitively respond to species of interest, reference electrodes which control the potentials of working electrodes, and counter electrodes which pass the electrical currents generated on the working electrodes. Alternatively, the reference and counter electrodes can be combined as one electrode to form a two-electrode system. The working electrode is typically constructed of a sensing layer, which is in direct contact with the conductive material of the electrode, and a diffusion-limiting membrane layer on top of the sensing layer. The reference electrode is typically composed of Ag/AgCl, which is fabricated via screen printing or electroplating. However, the lifetime of a screen-printed Ag/AgCl reference electrode is typically limited in an in vivo amperometric sensor due to dissolution of the AgCl into the surrounding tissue.

As a result, the sensor's life as a whole is often limited by the amount of Ag/AgCl available on the sensor's reference electrode. Although increasing the level of Ag/AgCl loaded on the reference electrode can prolong the lifetime of the reference electrode, the small and compact size of an implantable biosensor prevents from doing so.

Therefore, there remains a need for providing a reference electrode having an extended lifetime that is suitable for long term use in an implantable biosensor. The present invention addresses this need.

SUMMARY OF THE INVENTION

The present application provides Ag/AgCl based reference electrodes having an extended lifetime that are suitable for use in long term amperometric sensors. Electrochemical sensors equipped with reference electrodes described herein demonstrate considerable stability and extended lifetime in a variety of conditions.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 4 shows a schematic diagram of an embodiment of an analyte sensor according to the present invention;

FIGS. 5A-5B show a perspective view and a cross sectional view, respectively of another embodiment an analyte sensor;

Figure 1:
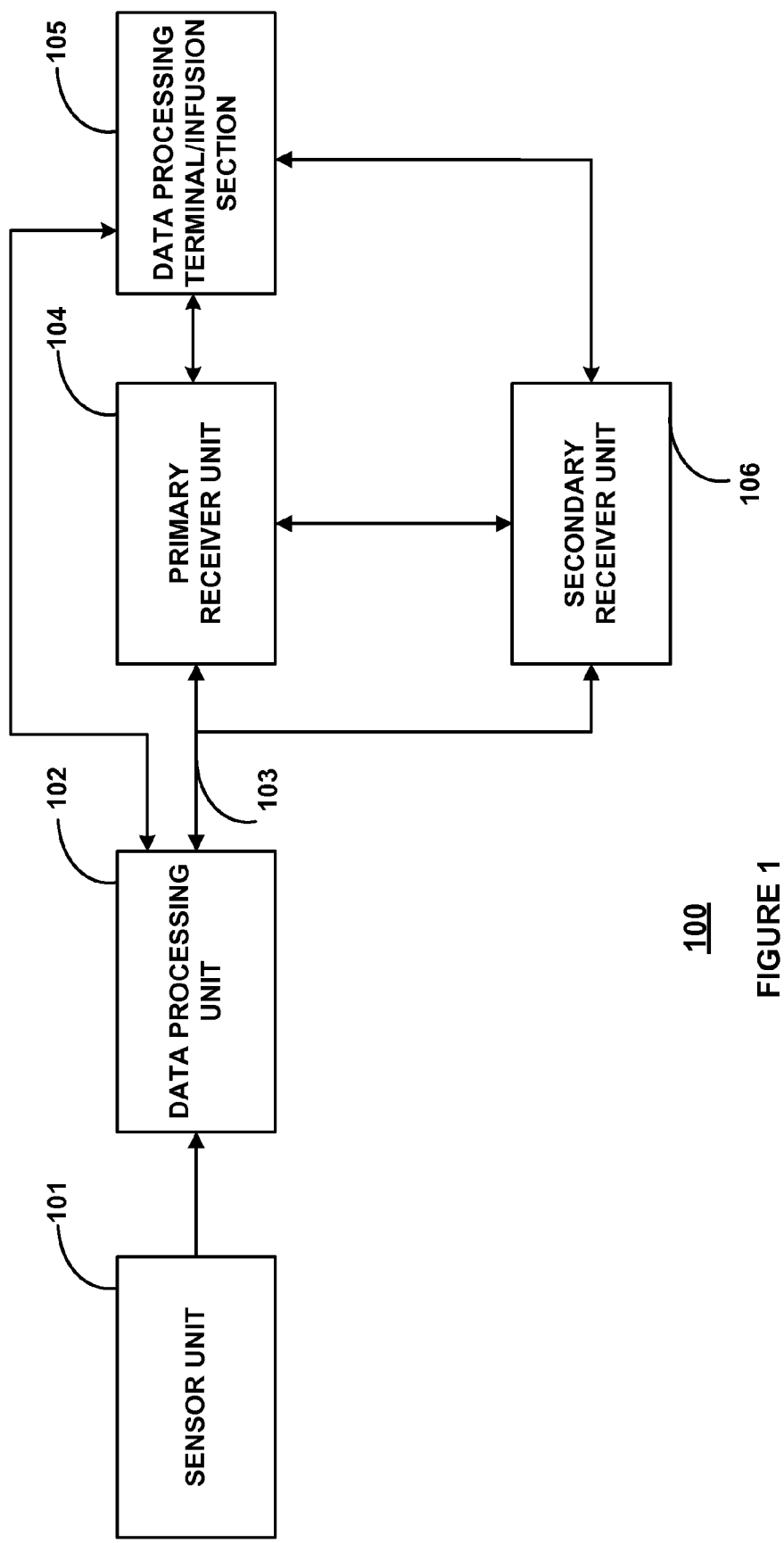
FIG. 1 shows a block diagram of an embodiment of a data monitoring and management system according to the present invention.

The figures shown herein are not necessarily drawn to scale, with some components and features being exaggerated for clarity.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Reference Electrodes

In general, electrochemical sensors include a working electrode, a reference electrode and a counter electrode. A working electrode is an electrode at which the analyte, or a compound whose level depends on the level of the analyte, is electrooxidized or electroreduced with or without the agency of an electron transfer agent. A reference electrode refers to an electrode that functions as a redox electrode that provides for measuring or controlling the potential of the working electrode. The term reference electrode includes both a) reference electrodes and b) reference electrodes that also function as counter electrodes (i.e., counter/reference electrodes), unless otherwise indicated.

In order for an electrochemical sensor to function properly over an extended period of time the reference electrode must be able to maintain a stable potential over the lifetime of the measurement period. In the case of an implanted continuous and/or automatic in vivo monitoring system, this period could range from hours, to day, and months, or more. The reference electrodes described herein comprise silver metal (Ag) and its silver salt (AgCl) deposited on a solid substrate. However, due to the solubility of AgCl in an aqueous environment, a reference electrode comprising Ag/AgCl as the reference element will be subject to dissolution over an extended period of in vivo implantation.

In order to increase the period of time in which an electrochemical sensor may remain implanted in vivo, the present invention provides reference electrodes having an extended Ag/AgCl lifetime that are suitable for use in long term amperometric sensors. In some embodiment, a portion of the Ag/AgCl of the reference electrode is covered with an impermeable dielectric layer in order to protect the Ag/AgCl underneath the layer from direct contact with the aqueous environment. In other embodiment, the Ag/AgCl of the reference electrode is covered with a permselective coating that provides for low permeability of the AgCl to the surrounding aqueous environment. In other embodiments, a brief electric potential is applied to the Ag/AgCl reference electrode in order to convert the silver metal (Ag) to its silver salt (AgCl) to replenish the silver salt that has been lost due to dissolution.

Such Ag/AgCl based reference electrodes having an extended lifetime are described in greater detail below.

Reference Electrode Having a Dielectric Layer

As noted above, in some embodiments, in order to increase the lifetime of an Ag/AgCl reference electrode, a portion of the lateral surface of the Ag/AgCl is covered with a dielectric layer that protects the Ag/AgCl underneath from dissolution into the environment and provides a reservoir of Ag/AgCl. As such, the reservoir of Ag/AgCl under the dielectric layer is capable of replacing the AgCl that is dissolved in the aqueous environment following implantation of at least a portion of the reference electrode subcutaneously in a patient. By "covered" is meant that the layer of dielectric material is disposed on the lateral surface the Ag/AgCl, thereby covering a portion of the surface of the Ag/AgCl and providing an exposed portion of the lateral surface of the Ag/AgCl.

The term dielectric layer broadly refers to a thin-film structure of dielectric material deposited on at least a portion of the Ag/AgCl of a reference electrode. Most dielectric materials are solid. Examples include porcelain (ceramic), mica, glass, plastics, and the oxides of various metals. A suitable dielectric layer may be composed of, for example, $Al_2O_3$, $SiO_2$, $HfO_2$, $ZrO_2$, $TiO_2$, $La_2O_3$, $Y_2O_3$, $Gd_2O_3$, $GeO_2$, $SrTiO_3$, metal silicates (e.g., $Hf_xSi_yO_z$) and/or metal aluminates (e.g., $Hf_xAl_yO_z$).

In general, the dielectric layer will cover at least a portion of the Ag/AgCl sufficient to provide a reservoir of Ag/AgCl underneath the dielectric layer. The dielectric layer is disposed on at least about 5% or more of the lateral surface of the Ag/AgCl, including up to about 95% of the lateral surface of the Ag/AgCl. In some embodiments, the dielectric layer covers at least about 10%, including about 20%, about 30%, about 40%, about 50%, about 60%, about 70%, about 80%, and about 90%, of the lateral surface of the Ag/AgCl.

Figure 6A:
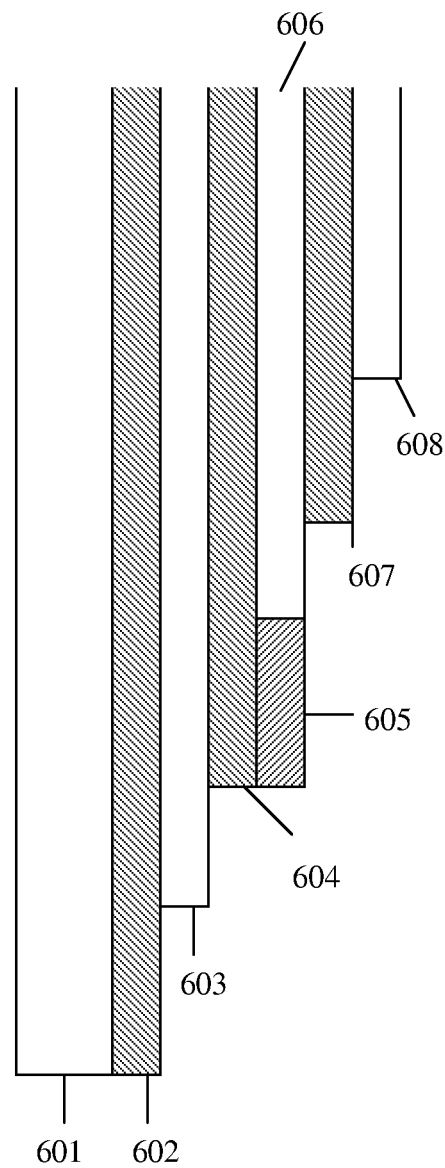
FIG. 6A is a cross-sectional schematic layout of an electrode and dielectric layers (polyester substrate (601), carbon working electrode layer (602), dielectric layer (603), carbon conductive trace for reference electrode (604), Ag/AgCl reference electrode pad (605), dielectric layer (606), carbon counter electrode (607), and dielectric layer (608))
Figure 6B:
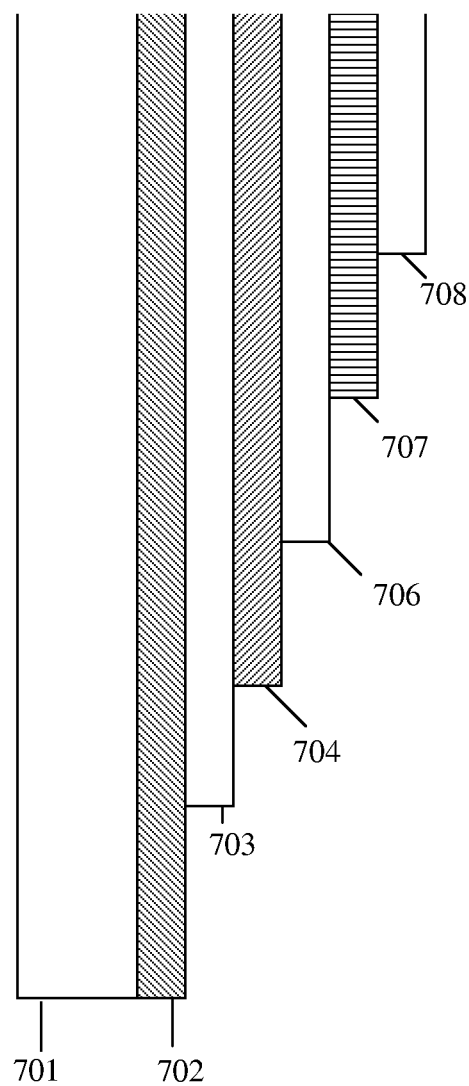
FIG. 6B is a cross-sectional schematic layout of an electrode and dielectric layer covering the Ag/AgCl (polyester substrate (701), carbon working electrode layer (702), dielectric layer (703), Ag/AgCl reference electrode pad (704), dielectric layer (706), carbon counter electrode (707), dielectric layer (708))

For example, as shown in FIG. 6B, in one aspect, the sensor 500 (such as the sensor unit 101 FIG. 1), includes a substrate layer 701, and a first conducting layer 702 such as carbon, gold, etc., disposed on at least a portion of the substrate layer 701, and which may provide the working electrode. Also disposed on at least a portion of the first conducting layer 702 is a sensing layer.

A first insulation layer such as a first dielectric layer 703 is disposed or layered on at least a portion of the first conducting layer 702, and further, a Ag/AgCl conducting layer 704 may be disposed or stacked on top of at least a portion of the first insulation layer (or dielectric layer) 703.

A second insulation layer 706 such as a dielectric layer in one embodiment may be disposed or layered on at least a portion of the Ag/AgCl layer 704. Further, a third conducting layer 707 may provide the counter electrode. It may be disposed on at least a portion of the second insulation layer 706. Finally, a third insulation layer 708 may be disposed or layered on at least a portion of the third conducting layer 707. In this manner, the sensor may be layered such that at least a portion of each of the conducting layers is separated by a respective insulation layer (for example, a dielectric layer). The embodiment of FIG. 6B show the layers having different lengths. Some or all of the layers may have the same or different lengths and/or widths.

Reference Electrode having a Permaselective Coating

In some embodiments, in order to increase the lifetime of an Ag/AgCl reference electrode, at lest a portion of the lateral surface of the Ag/AgCl is covered with a permselective coating that protects the Ag/AgCl underneath from dissolution into the environment and provides a reservoir of Ag/AgCl. As such, the permselective coating prevents the Ag/AgCl underneath to dissolve into the aqueous environment, thereby providing a constant level of Ag/AgCl to maintain a stable potential over the lifetime of the measurement period, such as following implantation of at least a portion of the reference electrode subcutaneously in a patient.

In some embodiments the permselective coating is a copolymer of polyvinyl pyridine and styrene. In such embodiments, the polyvinyl pyridine will be loaded with at 5% styrene, including about 10%, about 12%, about 15%, about 17%, and about 20% or more. In some embodiments, the permselective layer comprises polyvinyl pyridine with about a 10% loading of styrene. Suitable copolymers include, poly(2-vinylpyridine-co-styrene), poly(4-vinylpyridine-co-styrene), and the like.

Such a permselective layer for use in limiting the dissolution of the Ag/AgCl of the reference electrode into the aqueous environment may be different that a flux limiting membrane applied over the sensing layer of the working electrode that limits the flux of analytes to the enzymes present in the sensing layer. As such, in some embodiments, the electrode will further comprise a second flux limiting membrane.

In Situ Renewal of Ag/AgCl of a Reference Electrode

In some embodiments level of AgCl on a reference electrode of a electrochemical sensor is replenished by applying an electrical potential across the reference electrode and another electrode for a period of time sufficient to convert Ag to AgCl in order to replenish the level of AgCl present on the reference electrode. In general, following implantation of at least a portion of the reference electrode subcutaneously in a patient, a portion of the AgCl present on the reference electrode will dissolve into the aqueous environment. As a result of the loss of AgCl, the electrochemical sensor will not be able to maintain a stable potential over the lifetime of the measurement period. An electrical potential applied to the reference electrode will result in the oxidation of the silver metal (Ag) portion of to provide $Ag^+$. The $Ag^+$ will then combine with $Cl^-$ present in the in vivo environment to form silver salt (AgCl) on the reference electrode, thereby replenishing the level of AgCl present on the reference electrode.

The electrical potential applied to the reference electrode must be at a sufficient level and for a sufficient period of time to provide for conversion of a sufficient level of Ag to $Ag^+$. The electrical potential applied will include at least about +50 mV, such as about +75 mV, about +100 mV, +125 mV, +150 mV, +175 mV, +200 mV, +250 mV, etc. In addition, the electrical potential is applied for a duration of at least 30 seconds, including about 45 seconds, about 1 minute, about 2 minutes, about three minutes or more. It will be appreciated by one of skill in the art that the level as well the duration of the electrical potential applied may be adjusted to provide a suitable amount of Ag conversion. For example, a low level electrical potential, such as +50 mV, with longer duration, such as 2 minutes. As the level of electrical potential is increased, the duration at which the electrical potential is applied may be decreased.

The application of the electrical potential can also be repeated one or more times during the period in which a portion of the reference electrode is placed subcutaneously in a patient. This period may last from about 1 day to about 3 days, about 5 days, about 1 week, about 2 weeks, about 3, weeks, about 1 month, about 2 months or more. As such, the application of the electrical potential may be repeated about 2 times, about 3 times, about 4 times, about 5 times, about 6 times, about 7 times, about 8 times, about 9 times, about 10 times, or more. It will be appreciated by one skilled in the art that the number of times an electrical potential may be applied to the reference electrode in order to replenish the level of AgCl present on the reference electrode will be limited by the level of Ag present on the reference electrode that is available for conversion to AgCl.

Electrochemical Sensors

Generally, embodiments of the present invention relate to methods and devices for detecting at least one analyte, such as glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinedable devices, systems and methods and/or transferring data between an in vivo continuous system and a BG meter system.

An electrochemical sensor that includes at least one Ag/AgCl reference electrode having an extended lifetime can be formed on a substrate. The sensor may also include at least one counter electrode (or counter/reference electrode) and/or at least one reference electrode. An "electrochemical sensor" is a device configured to detect the presence and/or measure the level of an analyte in a sample, via an electrochemical oxidation or reduction reaction on the sensor, or via a sequence of chemical reactions where at least one of the chemical reactions is an electrochemical oxidation or reduction reactions on the sensor. These reactions are transduced to an electrical signal that can be correlated to an amount, concentration, or level of an analyte in the sample.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject invention having an Ag/AgCl reference electrode having an extended lifetime may be configured for monitoring the level of the analyte over a time period which may range from minutes, hours, days, weeks, to months, or longer.

Of interest are analyte sensors, such as glucose sensors, having an Ag/AgCl reference electrode having an extended lifetime, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month or more. Future analyte levels may be predicted based on information obtained, e.g., the current analyte level at time $t_0$, the rate of change of the analyte, etc. Predictive alarms may notify the user of a predicted analyte levels that may be of concern in advance of the user's analyte level reaching the future level. This provides the user an opportunity to take corrective action.

FIG. 1 shows a data monitoring and management system such as, for example, an analyte (e.g., glucose) monitoring system 100 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or a bidirectional communication device. A docking cradle may recharge a powers supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element such as adhesive or the like to secure it to the user's body. A mount (not shown) attachable to the user and mateable with the unit 102 may be used. For example, a mount may include an adhesive surface. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include an analog interface section including and RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone™ or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements), while avoiding potential data collision and interference.

Figure 2:
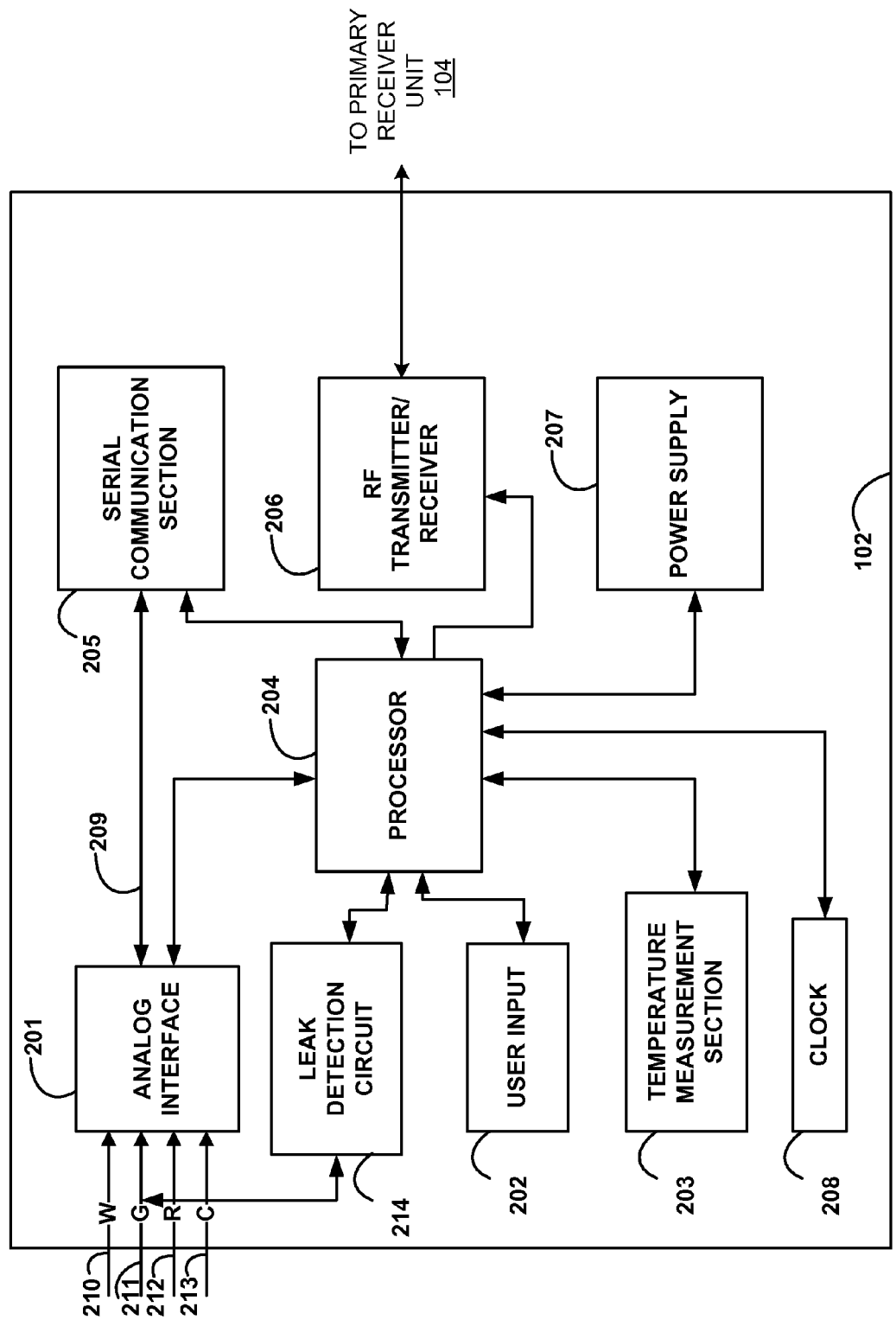
FIG. 2 shows a block diagram of an embodiment of the transmitter unit of the data monitoring and management system of FIG. 1.

FIG. 2 shows a block diagram of an embodiment of a data processing unit of the data monitoring and detection system shown in FIG. 1. User input and/or interface components may be included or a data processing unit may be free of user input and/or interface components. In certain embodiments, one or more application-specific integrated circuits (ASIC) may be used to implement one or more functions or routins associated with the operations of the data processing unit (and/or receiver unit) using for example one or more state machines and buffers.

As can be seen in the embodiment of FIG. 2, the sensor unit 101 (FIG. 1) includes four contacts, three of which are electrodes—work electrode (W) 210, reference electrode (R) 212, and counter electrode (C) 213, each operatively coupled to the analog interface 201 of the data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, etc.

Figure 3:
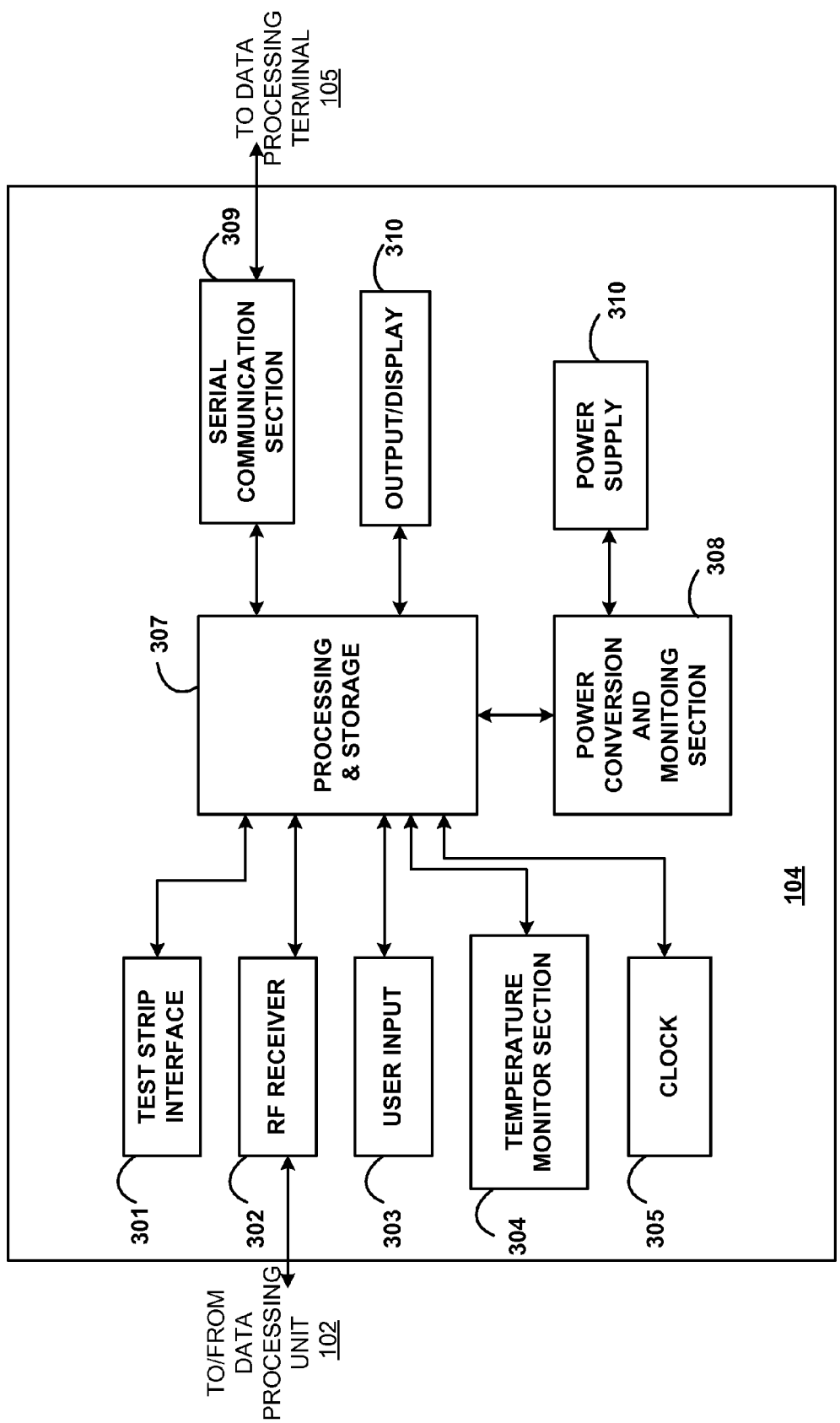
FIG. 3 shows a block diagram of an embodiment of the receiver/monitor unit of the data monitoring and management system of FIG. 1.

FIG. 3 is a block diagram of an embodiment of a receiver/monitor unit such as the primary receiver unit 104 of the data monitoring and management system shown in FIG. 1. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care, Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 105, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 105, or the data processing terminal/infusion section 105.

Additional detailed descriptions are provided in U.S. Pat. Nos. 5,262,035; 5,264,104; 5,262,305; 5,320,715; 5,593,852; 6,175,752; 6,650,471; 6,746,582, and in application Ser. No. 10/745,878 filed Dec. 26, 2003 entitled "Continuous Glucose Monitoring System and Methods of Use", each of which is incorporated herein by reference.

FIG. 4 schematically shows an embodiment of an analyte sensor in accordance with the present invention. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor unit 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

A first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, as described herein having an extended lifetime, which includes a layer of silver/silver chloride (Ag/AgCl).

A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be one the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analyte, such as oxygen, that can be directly electrooxidized or electroreduced on the working electrode. For these analytes, each working electrode includes a sensing layer (see for example sensing layer 408 of FIG. 5B) proximate to or on a surface of a working electrode. In many embodiments, a sensing layer is formed near or on only a small portion of at least a working electrode.

The sensing layer includes one or more components designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided).

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, such as glucose oxidase, lactate oxidase, or laccase, respectively, and an electron transfer agent that facilitates the electrooxidation of the glucose, lactate, or oxygen, respectively.

In other embodiments the sensing layer is not deposited directly on the working electrode. Instead, the sensing layer 64 may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2, 2'-bipyridines, such as 4,4'-dimethoxy-2,2'-bipyridine. Derivatives of 1,10-phenanthroline for complexation with the osmium cation include but are not limited to 4,7-dimethyl-1, 10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (Abbott Diabetes Care) that works at a gentle oxidizing potential, e.g., a potential of about +40 mV vs. Ag/AgCl. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

In certain embodiments, the sensing system detects hydrogen peroxide to infer glucose levels. For example, a hydrogen peroxide-detecting sensor may be constructed in which a sensing layer includes enzyme such as glucose oxides, glucose dehydrogensae, or the like, and is positioned proximate to the working electrode. The sensing layer may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. One advantage of an implantable sensor having a rigid substrate is that the sensor may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the patient during operation of the sensor. However, the barb is typically small enough so that little damage is caused to the subcutaneous tissue when the sensor is removed for replacement.

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Insertion Device

An insertion device can be used to subcutaneously insert the sensor into the patient. The insertion device is typically formed using structurally rigid materials, such as metal or rigid plastic. Preferred materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, such as a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that operate the sensor and the analyte monitoring device system. The electronic components of the sensor control unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, such as transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, such as but not limited to glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a sensor. In these embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically about 50 to 250 mg/dL, preferably about 40-300 mg/dL and ideally 30-400 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Reference Electrode Having a Dielectric Cover Layer

FIG. 6A shows a glucose sensor design with three electrodes that are formed by screen-printing on a polyester substrate. The conductive traces are separated by dielectric layers that are also formed by screen printing. The Ag/AgCl pad has an area of about 0.1 mm$^2$, and a thickness of about 5 µm. The total load of AgCl is about 400 ng. Clinical studies using sensors of this design have shown that the sensor output current becomes noisy 3-4 days after implantation. Subsequent in-vitro studies confirmed this phenomenon. Coulometric experiments showed that, whenever a sensor's output current became noisy, there was almost no AgCl left on its Ag/AgCl reference electrode.

Figure 7:
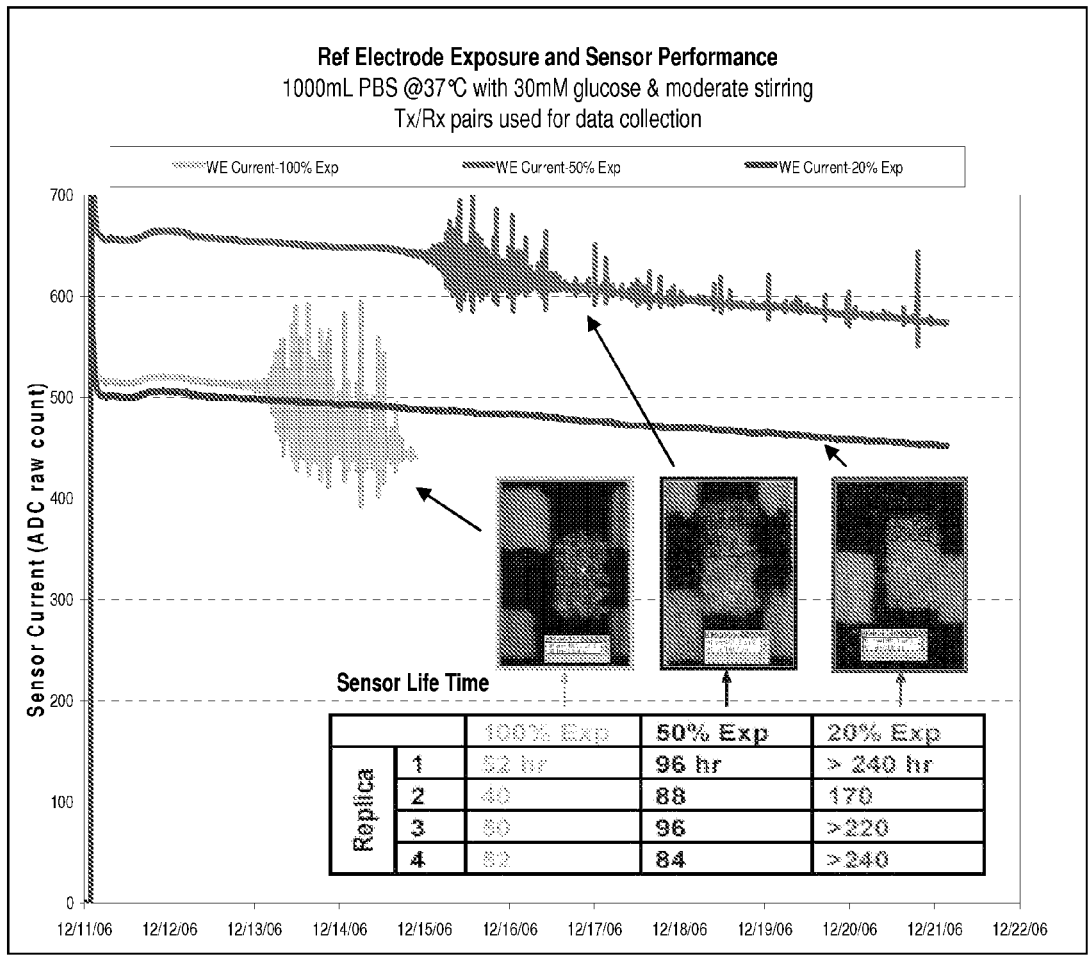
FIG. 7 shows sensor life dependence on the coverage area of Ag/AgCl of reference electrode by dielectric.

To improve the sensor performance, a series of sensors were fabricated with the Ag/AgCl pad covered partially by a layer of dielectric. Three sets of sensors with exposed Ag/AgCl areas of approximately 20%, 50%, and 100% (n=4 for each case) of the relatively constant total electrode area were tested in vitro. The results are illustrated in FIG. 7. It can be seen that the sensor life overall was greatly prolonged by covering a portion of the Ag/AgCl of the reference electrode with a dielectric.

Based on this result, a new sensor design with a one-layer less structure is shown schematically in FIG. 6B. By using only the Ag/AgCl trace, this design not only eliminates one screen-printing step, but also ensures the consistency of reference electrode layout.

Example 2

Reference Electrode Having a Permselective Layer

Figure 8:
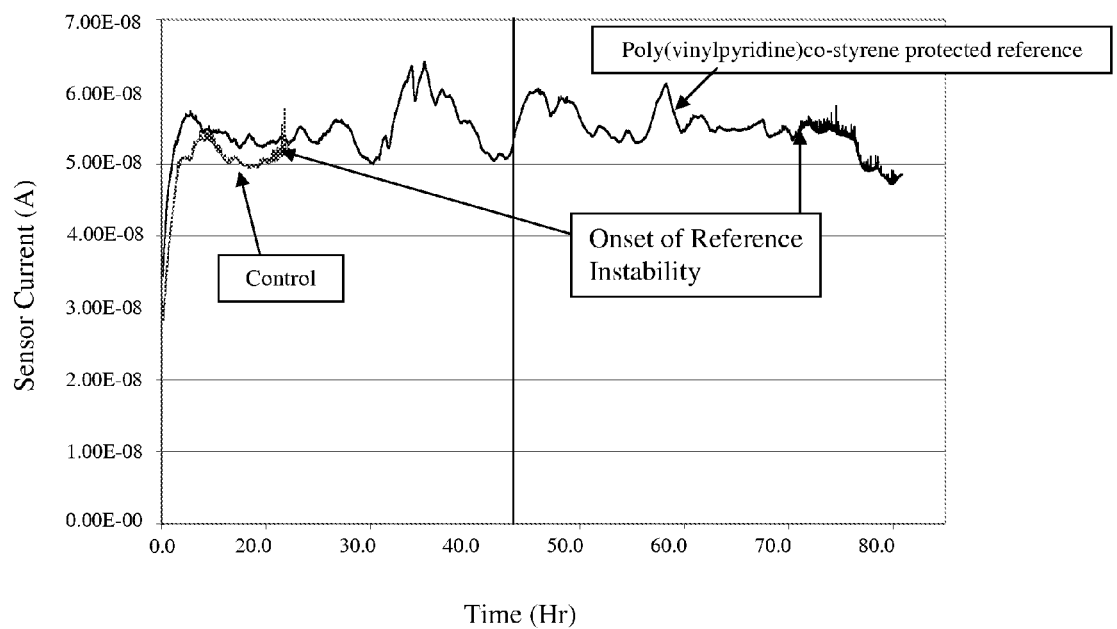
FIG. 8 shows increase in sensor life at 66° C. as a result of application of a permselective coating over Ag/AgCl.

A permselective coating (in addition to the overlying glucose flux-limiting membrane) can extend reference electrode lifetime. Experiments were performed with a localized coating of poly(vinylpyridine-co-styrene) with 10% loading of styrene over the Ag/AgCl reference element of the reference electrode. This material has a much lower permeability than the standard (control) glucose flux-limiting membrane. FIG. 8 shows accelerated aging studies (at 66° C.) of such an electrode, compared to a control (non-protected) reference electrode.

Note electrode lifetime (the time until onset of noise in the signal) is significantly improved in the protected electrode, from approximately 18 hours to 120 hours, or about a 6 fold increase. Furthermore, this protected electrode is expected to have a substantially longer lifetime at the subcutaneous temperature of about 34° C.

Example 3

Figure 9:
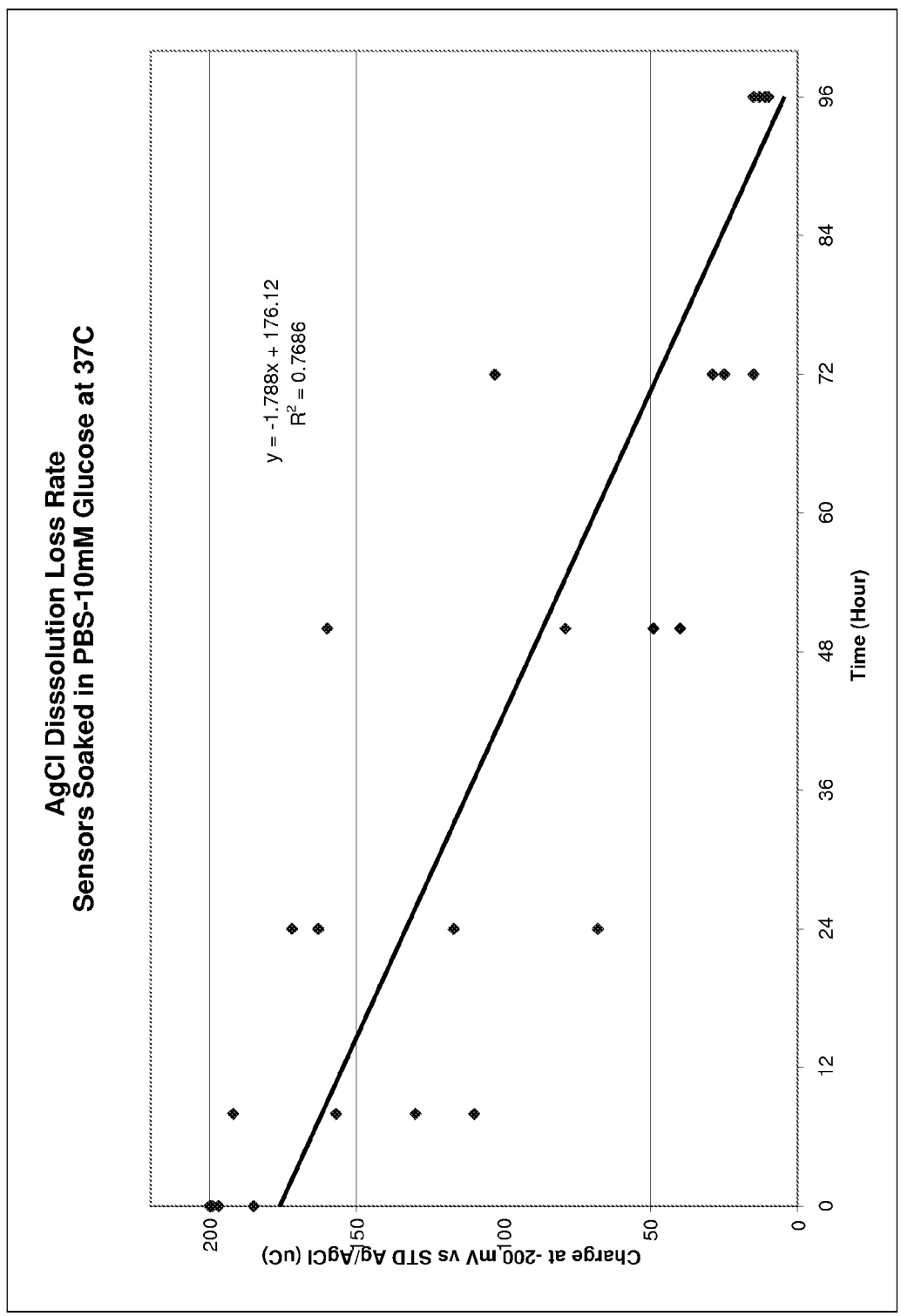
FIG. 9 shows the AgCl dissolution rate of a standard Ag/AgCl reference electrode as determined by coulometric method.

Renewing Ag/AgCl Reference Electrode In Situ with an Applied Electrical Potential The reference electrode of the experimental sensors was formed by screen printing a Ag/AgCl pad with an area of about 0.1 mm$^2$, and a thickness of about 5 µm. The total load of AgCl and Ag are about 400 ng and 1000 ng, respectively. The total electrochemically accessible AgCl and Ag are equivalent to 200 µC and 500 µC, respectively. In order to evaluate the charge injection frequency, the dissolution rate of AgCl was first determined in-vitro in PBS using standard coulometric technique. As seen in FIG. 9, AgCl dissolves at an average rate of about 50 µC per day. The variation in the charge values is due to the variation of the reference electrode pad areas caused by the screen printing resolution limitation.

Figure 10A:
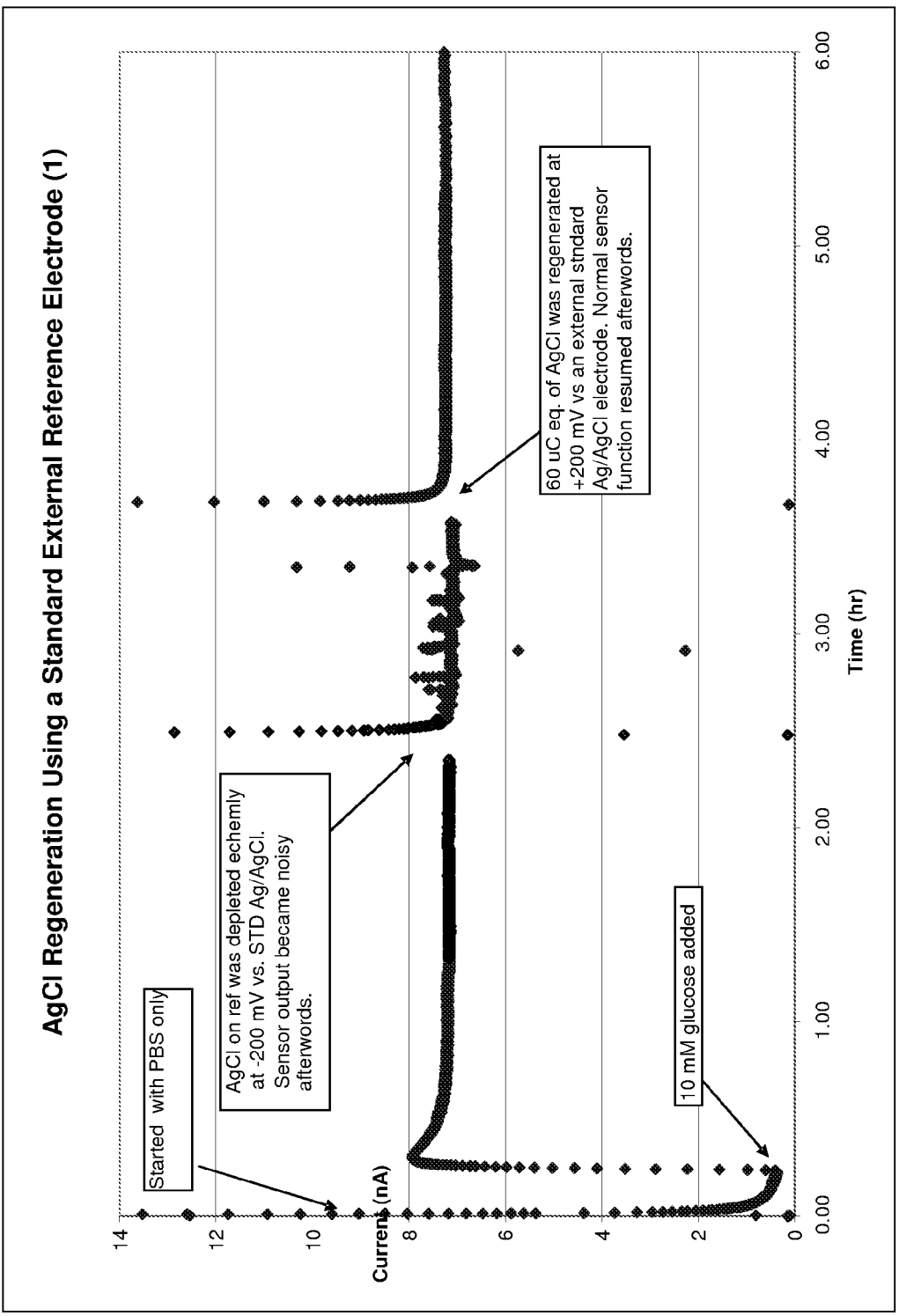
FIGS. 10A-10B show regeneration of AgCl using external reference and counter electrodes by application of electrical potential to convert Ag to AgCl (FIG. 10A shows the first six hours of the experiment and FIG. 10B shows the same experiment between hours 25 and 55)
Figure 10B:
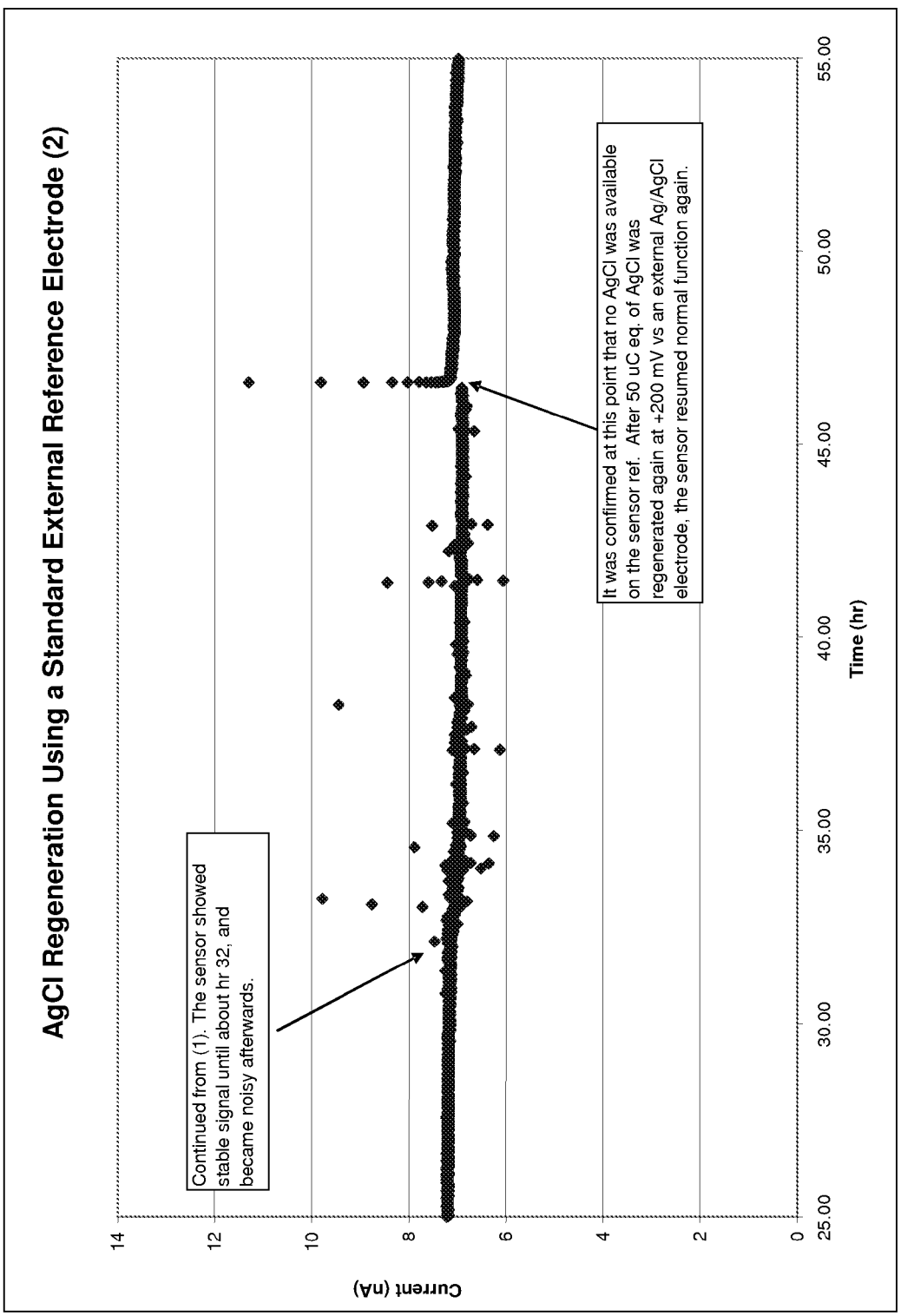

With a potential of +200 mV against a commercial standard Ag/AgCl electrode (Bioanalytical Systems, Inc.), AgCl was successfully regenerated repeatedly on the sensor's reference electrode, as demonstrated in FIGS. 10A and 10B. In addition, it can be seen that the loss rate of the regenerated AgCl is about the same as the original AgCl from the screen printing ink.

Figure 11:
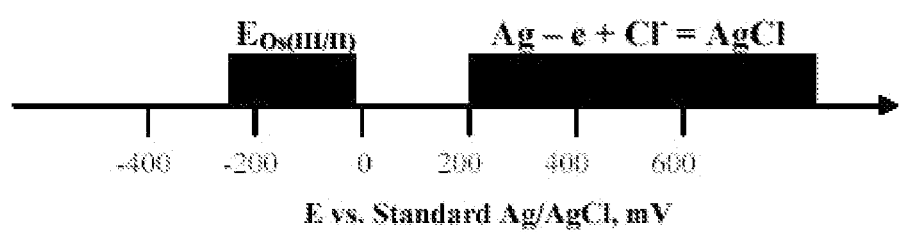
FIG. 11 shows Os (III/II) potential range vs. a standard Ag/AgCl reference electrode.

In order to regenerate AgCl in-situ, this invention utilizes the working electrode of a Navigator sensor as the reference electrode. The rationale is that the Os(III/II) redox couple present in the sensing chemistry should dominate the electrochemical potential of the electrode. In order to select a proper potential to regenerate AgCl using this electrode as a reference, the potential range of the Os(III/II) couple on the sensor's working electrode was first determined. Glucose and oxygen concentrations are the two variables in the in-vivo environment affecting the relative ratio of Os(III) and Os(II) which determines the electrode potential (per Nernst equation). High glucose and low oxygen concentrations would raise the Os(II) relative to Os(III), and this would shift the electrode potential negatively. It was found that the possible potential range of the Os couple against a standard Ag/AgCl is from 0 to −250 mV when varying glucose from 0 to 30 mM and $O_2$ from 20% to 2%. As shown in FIG. 11, a potential higher than +450 mV vs. Os(III/II) would be equivalent to +200 mV or higher vs. a standard Ag/AgCl electrode.

Figure 12:
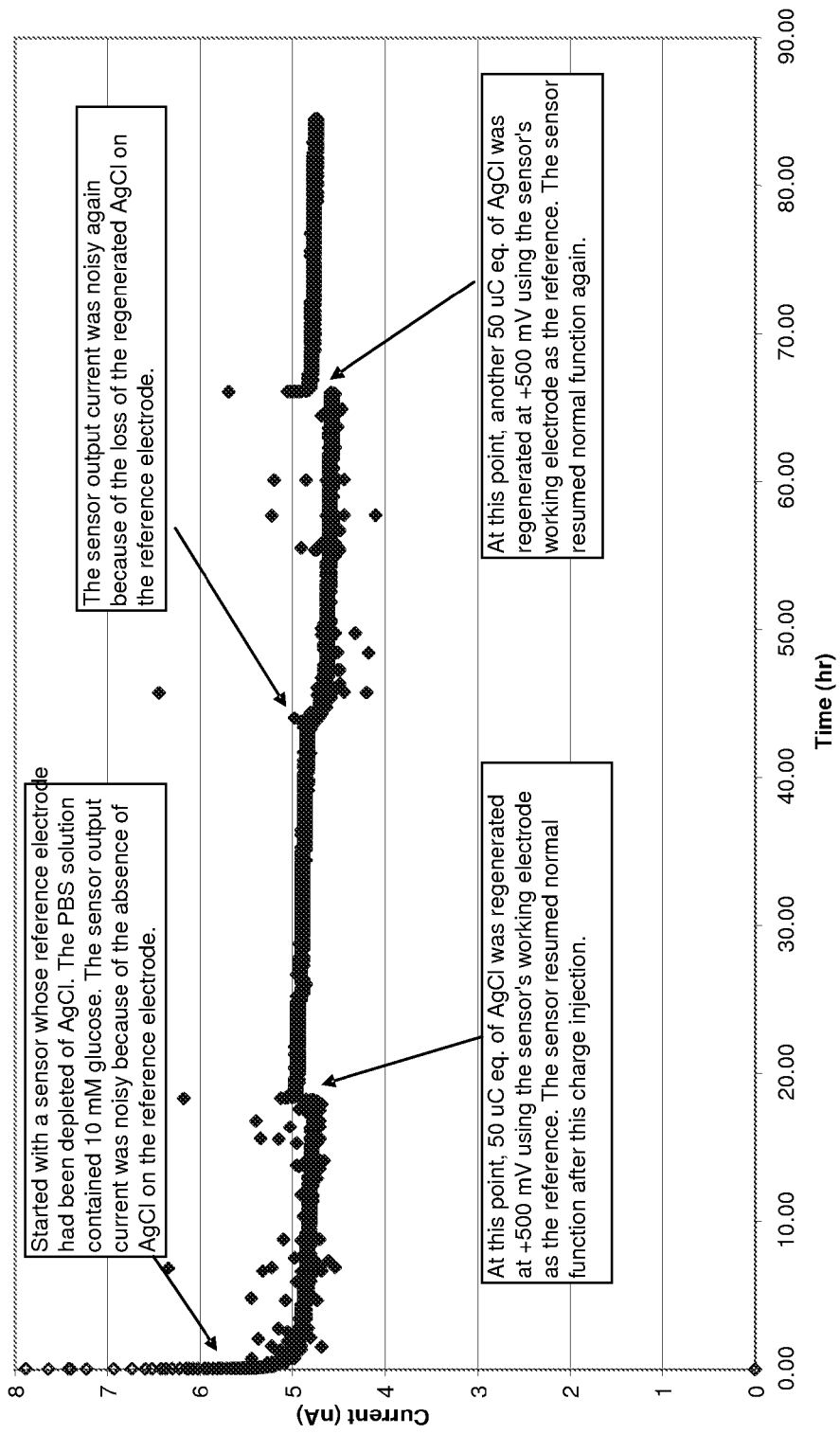
FIG. 12 shows regeneration of AgCl in-situ using the Navigator™ sensor's working electrode as the reference, and its counter as the counter electrode, by application of electrical potential to convert Ag to AgCl.

Based on this result, a potential of +500 mV vs. the working electrode was selected to regenerate AgCl on the sensor' reference electrode in-situ. As shown in FIG. 12, the results are the same as using external electrodes as shown in FIGS. 10A-10B. In both situations a stabilization of the signal was witnessed after the level of AgCl was replenished by application of electrical potential.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of replenishing a level of AgCl on a reference electrode of a electrochemical sensor, the method comprising:
   inserting a electrochemical sensor into skin of a patient, wherein the electrochemical sensor comprises a flexible substrate comprising
   (i) at least one working electrode comprising a sensing layer and a membrane disposed over the sensing layer, wherein the sensing layer comprises a mediator and an analyte responsive enzyme,
   (ii) at least one reference electrode comprising a layer of Ag/AgCl,
   (iii) at least one contact pad coupled to each of the working and reference electrodes, wherein the electrochemical sensor is adapted for implantation of a portion of the electrochemical sensor comprising the working and reference electrodes through skin;
   determining that AgCl on the reference electrode has become depleted while inserted in the patient; and
   applying an electrical potential across the reference electrode and another electrode of the sensor for a period of time sufficient to convert Ag to AgCl in order to replenish the level of AgCl present on the reference electrode, wherein the electrical potential to replenish AgCl present on the reference electrode is different from the oxidation potential of the mediator.

2. The method of claim 1, wherein said electrical potential to replenish AgCl is at least +50 mV.

3. The method of claim 1, wherein said electrical potential to replenish AgCl is at least +100 mV.

4. The method of claim 1, wherein said electrical potential to replenish AgCl is at least +200 mV.

5. The method of claim 1, wherein said electrical potential to replenish AgCl is applied for a duration of at least 30 seconds.

6. The method of claim 1, wherein said electrical potential to replenish AgCl is applied for a duration of at least 45 seconds.

7. The method of claim 1, wherein said electrical potential to replenish AgCl is applied for a duration of at least 1 minute.

8. The method of claim 1, wherein said application of electrical potential to replenish AgCl is repeated at least once.

9. The method of claim 1, wherein said application of electrical potential to replenish AgCl is repeated at least twice.

10. The method according to claim 1 wherein the electrical potential to replenish AgCl present on the reference electrode is from +200 mV to +600 mV.

11. The method according to claim 10, wherein the electrical potential to replenish AgCl present on the reference electrode is +500 mV.

12. The method according to claim 1, wherein the oxidation potential of the mediator is from −200 mV to +200 mV.

13. The method according to claim 1, wherein the mediator comprises osmium.

14. The method according to claim 1, wherein determining that AgCl on the reference electrode has become depleted comprises determining that sensor output current is noisy.

15. The method according to claim 1, wherein determining that AgCl on the reference electrode has become depleted comprises determining that no AgCl is present on the reference electrode.

16. The method according to claim 1, wherein the method further comprises determining that the replenished level of AgCl present on the reference electrode has become depleted.

17. The method according to claim 1, wherein determining that AgCl on the reference electrode has become depleted while inserted in the patient comprises determining that the sensor output current is noisy about 3 to 4 days after implantation.

* * * * *